United States Patent [19]

Dahlberg et al.

[11] Patent Number: 4,650,458
[45] Date of Patent: Mar. 17, 1987

[54] APPARATUS FOR THE MEASUREMENT OF FLUID FLOW

[75] Inventors: Bengt A. G. Dahlberg, Veberöd; Jan-Bertil Jeppsson, Lomma; Lars I. Ohlsson, Asarum; Tord B. Simonsson, Landskrona, all of Sweden

[73] Assignee: Gambro Lundia AB, Sweden

[21] Appl. No.: 742,586

[22] Filed: Jun. 7, 1985

[30] Foreign Application Priority Data

Jun. 18, 1984 [SE] Sweden .............................. 8403244

[51] Int. Cl.$^4$ .............................................. A61M 1/34
[52] U.S. Cl. ........................................ 604/5; 604/30; 604/246; 604/45; 604/126; 210/927; 210/136; 210/321.3
[58] Field of Search ............... 604/30, 5, 6, 4, 246, 604/247, 45, 126, 122, 123; 55/158; 210/927, 136, 472, 436, 433.2, 321.2, 321.3; 128/D3

[56] References Cited

U.S. PATENT DOCUMENTS

| | | | |
|---|---|---|---|
| 3,064,649 | 11/1962 | Fuson | 128/D3 |
| 4,013,072 | 3/1977 | Jess | 210/436 |
| 4,054,523 | 10/1977 | Ingenito et al. | 210/436 |
| 4,223,672 | 9/1980 | Terman et al. | 604/5 |
| 4,231,366 | 11/1980 | Schael | 604/4 |
| 4,243,530 | 1/1981 | Lehnhoff et al. | 210/472 |
| 4,275,726 | 6/1981 | Schael | 604/5 |
| 4,298,358 | 11/1981 | Ruschke | 210/436 |
| 4,303,068 | 12/1981 | Zelman | 604/5 |
| 4,412,916 | 11/1983 | Kell | 210/436 |
| 4,536,201 | 8/1985 | Brovsson et al. | 210/436 |

Primary Examiner—C. Fred Rosenbaum
Assistant Examiner—John D. Ferros
Attorney, Agent, or Firm—Lerner, David, Littenberg, Krumholz & Mentlik

[57] ABSTRACT

Apparatus is disclosed for the measurement and replacement of physiological fluids including a meter for measuring the amount of a physiological fluid flowing through the meter, a first conduit for continuously delivering the physiological fluid to the meter, a second conduit for replacing the measured amount of physiological fluid with a corresponding amount of a replacement fluid, and a pressure equalizer associated with the first conduit for equalizing the pressure in the physiological fluid flowing through the first conduit whereby the flow of the physiological fluid through the meter is substantially unaffected by pressure variations in the physiological fluid itself.

29 Claims, 5 Drawing Figures

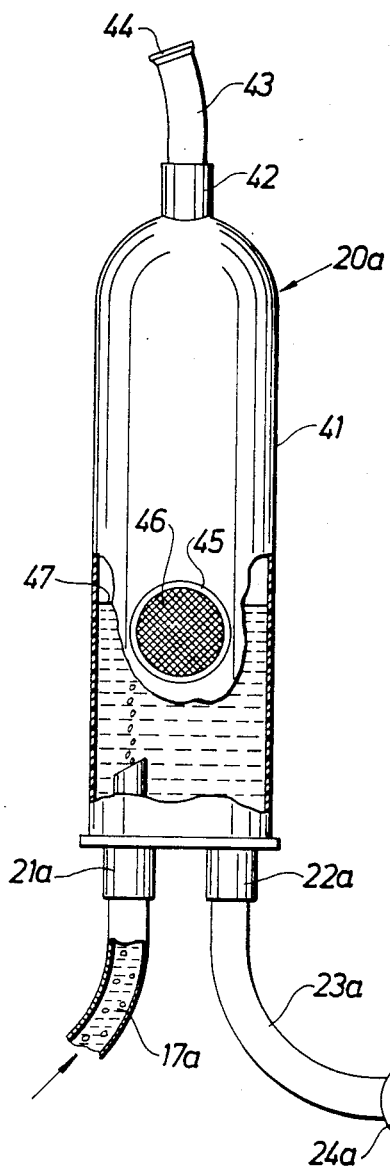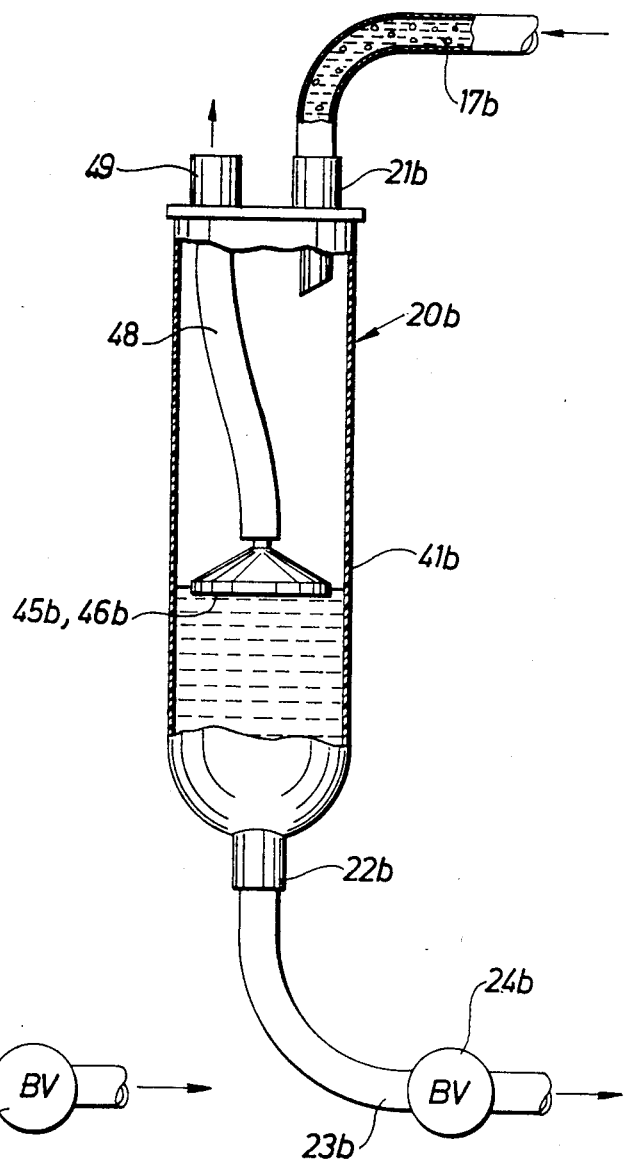

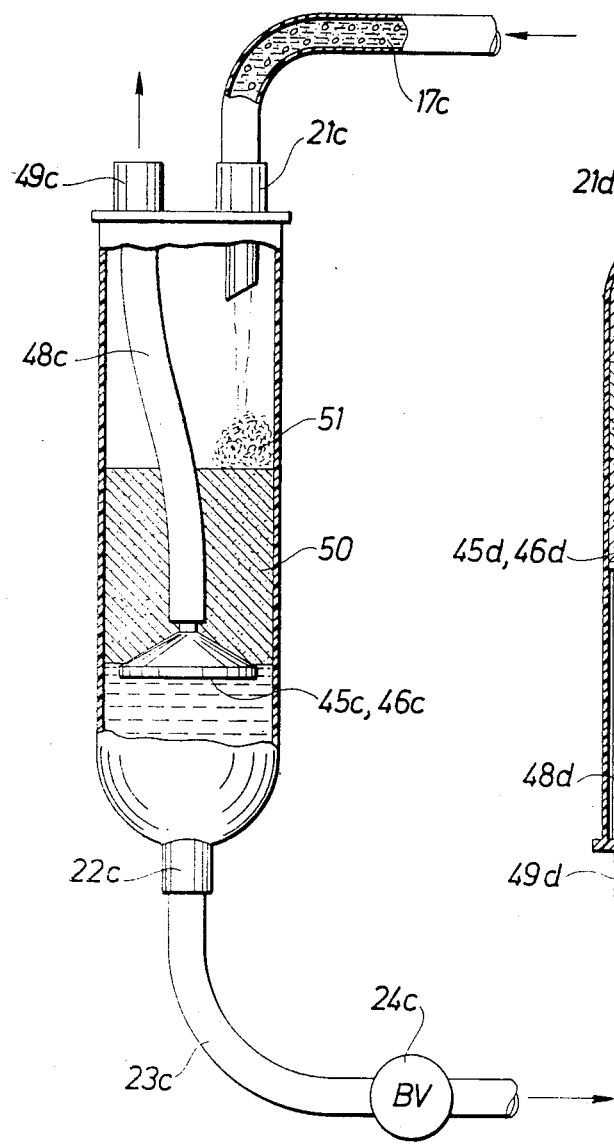

APPARATUS FOR THE MEASUREMENT OF FLUID FLOW

FIELD OF THE INVENTION

The present invention relates to blood filtering systems. More particularly, the present invention relates to blood filtering systems which includes means for withdrawing blood from a patient or from some other source, a filter for withdrawing a filtrate from the blood, and a suitable means for returning the remainder of the blood to the source together with any necessary replacement fluid. More particularly, the present invention relates to such apparatus in which a measuring device is arranged for measuring the amount of filtrate withdrawn therein.

The present invention is particularly intended to be used in connection with hemofiltration or plasmapheresis, in which a replacement fluid is supplied in place of the filtrate withdrawn in the filtering means. It will be clear, however, to those of ordinary skill in this art, that the invention can also be applied to other systems, such as in conjunction with hemodialysis, when the dialysis is combined with the removal of an ultrafiltrate.

BACKGROUND OF THE INVENTION

The overall process of hemofiltration which is carried out at the same time as preparation of a replacement fluid is shown, for example, in European Patent Application Nos. EP 0 042 939 and EP 0 087 171, respectively.

Plasmapheresis differs from hemofiltration primarily in that it requires a slightly more permeable membrane material so that even larger molecules can be filtered out therewith.

Examples of suitable hemofiltration membranes are described in Eurpoean Patent Application No. EP 0 046 816. Similarly, suitable membranes for plasmapheresis are described in European Patent Application No. EP 0 044 958. It will be clear, however, to those of ordinary skill in this art, that other membranes can also be used in conjunction with the realization of the present invention.

When in the past it has been necessary to measure the amounts of filtrate withdrawn in conjunction with processes such as hemofiltration or plasmapheresis it has been found to be quite difficult to carry out exact measurements due to variations in the pressure conditions and consequent varying flow conditions therein. In particular, specific problems were encountered on application of peristaltic pumps normally used in such processes. These types of pumps act from the outside of flexible blood tubes in a pulsating manner.

In accordance with a preferred embodiment of the apparatus of the present invention, a pressure equalizing device which comprises a gas-permeable but liquid-tight membrane is utilized. In this regard, reference is thus made to U.S. Pat. No. 4,198,971 which describes a drip chamber having a similar design. Such a drip chamber is also shown in European Patent No. 0 062 913. It again, however, does not relate to an overall system for measuring and replacing such fluids in connection with a filter or the like. Finally, German Patent Application No. DE 3243523A1 does show such a filtration system, which in this case includes a pair of expansion chambers 7 and 12 along with pumps 9 and 18 which are used to pump similar amounts of liquid to the liquid which is being filtered and discharged as well as replacement liquid.

SUMMARY OF THE INVENTION

In accordance with the present invention, improved apparatus for the measurement and replacement of physiological fluids has now been discovered which comprises measuring means for measuring the amount of the physiological fluid flowing therethrough, first conduit means for continuously delivering the physiological fluid to the measuring means, second conduit means for replacing that measured amount of physiological fluid with a corresponding amount of a replacement fluid, and pressure equalizing means associated with the first conduit means for equalizing the pressure in the physiological fluid flowing through the first conduit means whereby the flow of the physiological fluid through the measuring means is substantially unaffected by pressure variations in the physiological fluid.

In accordance with a preferred embodiment of the apparatus of the present invention, the physiological fluid is a filtrate withdrawn from a supply of blood. Preferably, the apparatus includes filter means for contacting with the supply of blood in order to produce the filtrate therefrom.

In accordance with another embodiment of the apparatus of the present invention, the pressure equalizing means is located at a point in the first conduit means substantially adjacent to the measuring means.

In accordance with another embodiment of the apparatus of the present invention, the pressure equalizing means includes bubble collection means for collecting any gas bubbles contained within the physiological fluid in order to prevent such gas bubbles from being delivered to the measuring means.

In accordance with another embodiment of the apparatus of the present invention, the apparatus includes pump means associated with the first conduit means and located at a point prior to (upstream from) the pressure equalizing means, whereby the pump means draws the physiological fluid through the first conduit means and through the pressure equalizing means into the measuring means. Preferably, the pump means comprises a peristaltic pump, whereby the pump means can contact the outer surface of the first conduit means for drawing the physiological fluid therethrough.

In accordance with another embodiment of the apparatus of the present invention, the measuring means comprises first measuring means, and the apparatus includes second measuring means for measuring the amount of the replacement fluid flowing into the second conduit means. In a preferred embodiment, the apparatus includes comparison means for comparing the amounts of the physiological fluid and the replacement fluid measured by the first and second measuring means, respectively.

In accordance with another embodiment of the apparatus of the present invention, the pressure equalizing means includes a housing and fluid level control means for maintaining the level of physiological fluid within that housing at a predetermined level therein. In another embodiment, the pressure equalizing means comprises first pressure equalizing means, and the apparatus includes second pressure equalizing means, associatd with the second conduit means for equalizing the pressure in the replacement fluid flowing through the second conduit means. In a preferred embodiment, at least one of the first and second pressure equalizing means includes a housing and fluid level control means for maintaining the level of the fluid within the housing at a predetermined level.

In accordance with a preferred embodiment of the apparatus of the present invention, the liquid level control means comprises membrane means having a first surface and a second surface, the first surface of the membrane means being in contact with the housing, whereby it is accessable to the fluid contained within the housing, and the second surface of the membrane means being exposed to the atmosphere, the membrane means being gas permeable and fluid impermeable, whereby the fluid level within the housing can thus be controlled by the passage of gas through the membrane means, i.e. in either direction. In a preferred embodiment, the housing includes an outer wall including the window, and the membrane means is contained within that window.

In accordance with a preferred embodiment of the apparatus of the present invention, the outer wall of the housing including a window means is vertically disposed, and the membrane means includes an upper end and a lower end, whereby the fluid level may be controlled substantially between the upper end and the lower end of the membrane means. Preferably, the membrane means is entirely enclosed within the housing.

In accordance with another embodiment of the apparatus of the present invention, the pressure equalizing means includes froth reduction means for reducing the creation of froth from the physiological fluid being handled therein.

In a preferred embodiment of the apparatus of the present invention, at least one of the first and second pressure equalizing means includes froth reduction means for reducing the creation of froth from the fluid being handled therein.

In accordance with another embodiment of the apparatus of the present invention, the apparatus includes temperature measuring means for measuring the temperature of the physiological fluid flowing through the first conduit means.

In accordance with a preferred embodiment of the apparatus of the present invention, the apparatus includes membrane conduit means connecting the second surface of the membrane means to the atmosphere. In a preferred embodiment, the membrane means is horizontally disposed within the housing. Preferably, the first surface of the membrane means is directed generally upwardly and the second surface of the membrane is directed generally downwardly. In a preferred embodiment, the membrane conduit means extends generally vertically downwardly from the second surface of the membrane means, whereby any condensate formed within the membrane conduit means runs downwardly along the membrane conduit means and away from the membrane means.

In accordance with a preferred embodiment of the apparatus of the present invention, the housing for the pressure equalizing means includes a fluid inlet at its upper end, in communication with the first conduit means. In a preferred embodiment, the housing includes froth reduction means for reducing the creation of froth from the fluid between the fluid inlet and the membrane means. Preferably, the housing for the pressure equalizing means includes a fluid outlet at the lower end thereof, the fluid outlet being in fluid communication with the first conduit means.

In accordance with the present invention, the aforementioned previously encountered problems are solved by the provision of a blood filtering system including the aforementioned pressure equalizing device, which is arranged in conjunction with the measuring device for equalizing the pressure in the flow of filtrate being conducted to the measuring device. As discussed, the pressure equalizing device is preferably arranged prior to the measuring device in the direction of flow, and preferably in close proximity to the measuring device. It is thus additionally insured that the pressure in the measuring device, and consequently also the flow therethrough, can be kept substantially constant so that in spite of variations in flow which do occur, continuous measurement is still readily achieved.

The pressure equalizing device of the present invention is also appropriately adapted to capture any gas bubbles which are created in the filtrate flow, since those too would disturb the measurement in a subsequent flow meter.

A practical design for the pressure equalizing device of this invention is to arrange it in the flow of filtrate downstream from a pump, which is in turn adapted to draw the filtrate from the filter, and to then press the filtrate through the pressure equalizing device and into the measuring device.

Furthermore, by employing a peristaltic pump in its known manner, whereby it acts from the outside of a flexible tube upon the filtrate conducted therein, contamination of the filtrate is thereby avoided.

It is within the scope of this invention to also employ another measuring device for measuring the amount of replacement fluid being supplied. A common measuring device may possibly be used for measurement of both the filtrate and of the replacement fluid. Such a device is suitably adapted to compare these respective measurements of fluid flow. In this manner, the amounts of fluid withdrawn and supplied can be safely checked in order to insure that they are in a specified proportional relationship with each other.

The second pressure equalizing device mentioned above can be arranged in a duct for the supply of replacement fluid back to the original source, such as the patient, and is appropriately located behind (downstream from) the measuring device for the replacement fluid.

Preferably, at least one of the pressure equalizing devices is provided with suitable means for automatic level control. This can be simply achieved by providing the device with a window to the outer atmosphere covered by a membrane which is gas-permeable but liquid-tight.

Such a window may be arranged on the outer wall of a pressure sleeve enclosing the pressure equalizing device, with the membrane being arranged in a vertical position, so that the fluid level therein will normally vary between the highest and lowest points of the membrane. Alternatively, the window can be arranged entirely within a housing enclosing the pressure equalizing device, one side of the membrane being adapted to be in contact with the interior of the housing, and the other side of the membrane adapted to be in contact with the outer atmosphere.

Preferably, at least one of these pressure equalizing devices, and most appropriately the first-mentioned one, is provided with means for the prevention of frothing or for breaking down froth already formed therein.

As a further safeguard of the accuracy of the measurements made with the measuring device, means may also be provided for measuring the temperature of the medium flowing therethrough. In this manner, the measured amount can then be compensated for on the basis of the change in density, which is obtained on the basis of variations in temperature. By way of example, it can be mentioned that, in connection with plasma, a temperature variation of approximately 2° C. results in a change of density of approximately 1 per mil.

BRIEF DESCRIPTION OF THE DRAWINGS

FIG. 2 is a side, elevational, partially sectional view of a pressure equalizing device for use in connection with the present invention;

FIG. 3 is a side, elevational, partially sectional view of another pressure equalizing device for use in connection with the present invention;

FIG. 4 is a side, elevational, partially sectional view of yet another pressure equalizing device for use in connection with the present invention; and FIG. 5 is side, elevational, partially sectional view of yet another pressure equalizing device for use in connection with the present invention.

DETAILED DESCRIPTION

Figure 1:
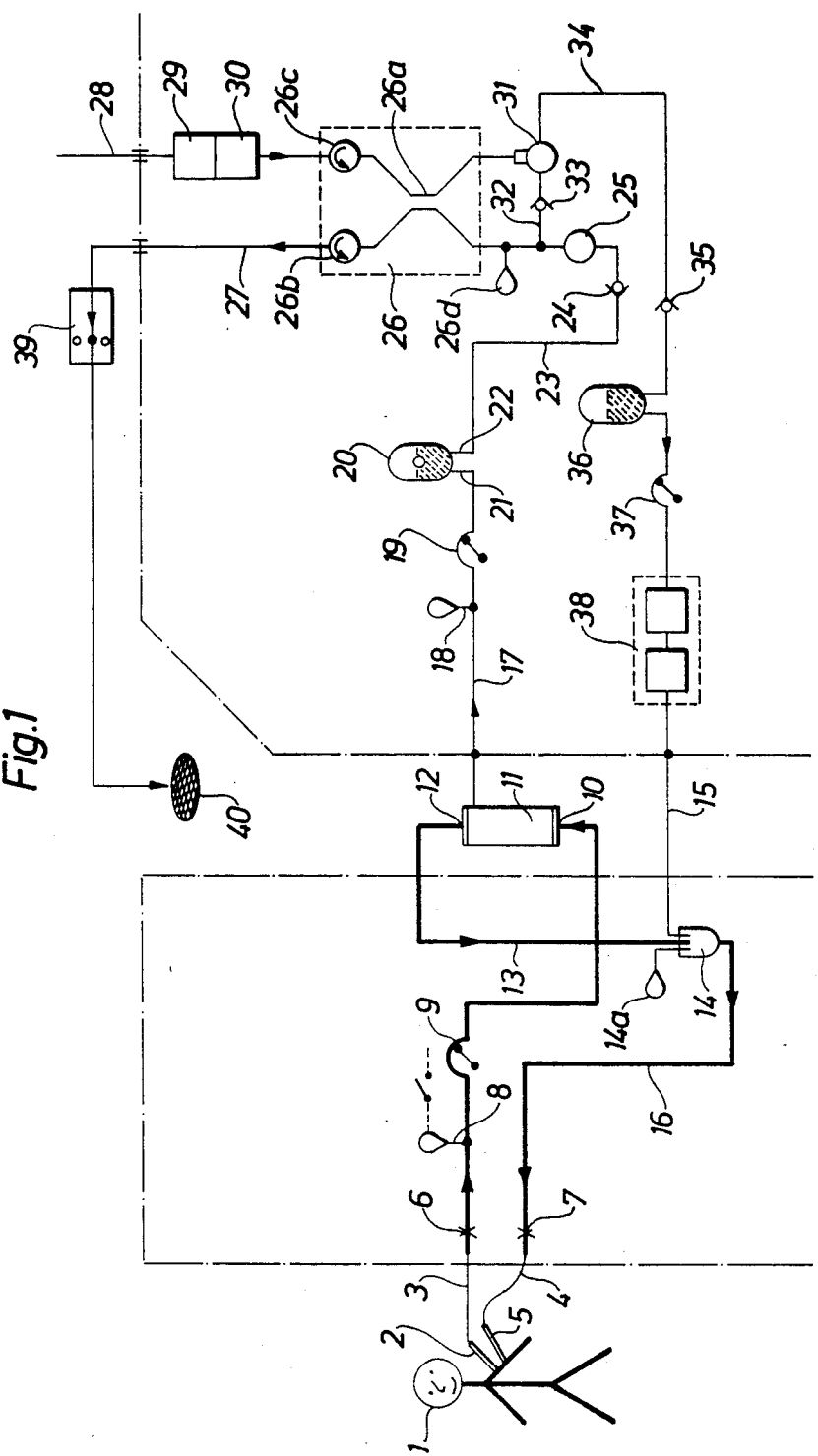
FIG. 1 is a schemative, flow diagram of a preferred overall system used in connection with the present invention.

Turning now to the drawings, in which like numerals refer to like portions thereof, in the block diagram shown in FIG. 1, a patient is designated 1. Blood is withdrawn from patient 1 by means of a cannula 2, and is then conducted through duct 3 into a blood treatment system. The blood is eventually returned to the patient through duct 4 and cannula 5. For reasons of safety, these ducts 3 and 4 can be shut off and opened with the help of clamps 6 and 7, respectively. After clamp 6, the blood passes an arterial pressure gauge 8, which is arranged upstream of a peristaltic pump 9, by means of which circulation of the blood in the system is achieved. From the pump 9 the blood is pressed through inlet 10 into filter 11, and then out of filter 11 through outlet 12.

The invention is particularly intended to be utilized in conjunction with hemofiltration or plasmapheresis, and the filter thus shown in FIG. 1 is a hemofilter or a plasmapheresis filter, respectively. The scope of the present invention, however, is not intended to be limited to these particular examples.

From outlet 12, the blood passes through duct 13 to drip chamber 14, which is coordinated with a venous pressure gauge 14a. A replacement fluid is also conducted to the drip chamber 14, through a duct 15. From the drip chamber, the blood mixed with replacement fluid is then conducted via duct 16, clamp 7 and cannula 5, back to the patient 1.

From the filter 11, filtrate is withdrawn through a duct 17, the pressure being measured by means of a pressure gauge 18. In order to draw the filtrate out of the filter 11, a pump 19 is utilized. This pump 19 is preferably a conventional peristaltic pump. The blood is then introduced into pressure equalizing device 20, which will be described in more detail in connection with FIGS. 2, 3, 4 and 5. The inlet to the pressure equalizing device 20 is designated 21, and the outlet is designated 22. Subsequently, the blood is conducted through duct 23, via check valve 24, and an appropriate controllable ultrafiltration valve 25, to a flow meter 26. This may be designed, for example, in accordance with European patent application No. EP 0 106 940, but other designs can of course be substituted therefor.

From meter 26, the filtrate passes through duct 27, either to a collecting point, if it is to be retained, or to a drain, 40.

A replacement fluid prepared in a separate set-up is supplied to the meter 26 through duct 28, conductivity meter 29, and temperature measuring device 30.

The meter 26 preferably comprises a first part 26a, which is used to measure the difference between flows in the ducts 27 and 28. Moreover, as a check, measurement of the individual flows in parts 26b and 26c can also take place. Furthermore, in order to effect possible adjustments in the measured flow on the basis of the temperature, meter 26 may be coordinated with a temperature measuring device 26d. From meter 26, the replacement fluid is delivered to a valve 31, which on the basis of the values measured on measuring devices 29 and 30 then conducts replacement fluid either to a by-pass duct 32, via check valve 33, and from there to discharge pipe 27, or to a duct 34, and via check valve 35, to pressure equalizing device 36, infusion pump 37, and possibly to a filter system 38, a duct 15, and then to drip chamber 14.

Finally, number 39 in FIG. 1 designates a valve which allows flow only when pressure exists in the system, but which immediately terminates the connection to drain 40 if the pressure measured at that point is greater than that in the remainder of the system. In such a case, an air gap is then created, so that it becomes impossible for fluid to be conducted from the drain 40 back into the system.

Referring next to FIG. 2, there is shown a pressure equalizing device 20a which is intended to act as the pressure equalizing device 20 in FIG. 1. In this case, the filtrate is supplied to the outer housing 41 of device 20a through duct 17a, and inlet 21a, and filtrate is withdrawn through the outlet 22a, duct 23a, and check valve 24a. A further connecting nipple 42 is located at the top of housing 41, with a connecting duct 43, which in this case is closed off by means of a weld 44. This connection is intended to be used for the withdrawal of samples, or for the supply of reagents or the like. Alternatively, it may be used for pressure measurement. Number 45 designates a window, which is covered by a membrane 46, which is preferably hydrophobic, gas-permeable but liquid-tight (liquid impermeable). This window, and the back pressure generated by check valve 24, permits the fluid level 47 to be automatically adjuste. If, at the outset, the fluid level is located above the window, it will thus drop gently owing to bubbles introduced therethrough, until it reaches the window. If the fluid level is initially lower, the accumulated gas is automatically released by being urged through the window, so that the fluid level then rises. As a result, the fluid level will then vary between the upper and lower edges of the window or membrane.

The device shown in FIG. 3 corresponds in principle to that in FIG. 2. For this reason, the same reference numerals have been used, but in this case with the addition of the letter "b". This device as a whole is designed 20b, and its housing is designated 41b. Similarly, the window with associated membrane have been designated 45b and 46b, respectively. Thus, filtrate is supplied through duct 17b and inlet 21b, and is withdrawn through outlet 22b, duct 23b, and check valve 24b. The differences between this device and that shown in FIG.

2 consist of the fact that in this case the window 45b, with its membrane 46b, is arranged horizontally inside the housing 41b, and is connected to the outer atmosphere through duct 48 and outlet 49.

Turning to the embodiment shown in FIG. 4, this device again corresponds substantially to that shown in FIG. 3. For this reason, the same reference numerals have once again been used, but in this case the letter "b" has been replaced by the letter "c". Thus, filtrate is supplied through duct 17c, and inlet 21c, and is withdrawn through outlet 22c, duct 23c, and check valve 24c. The accumulated gas is discharged through wndow 45c, with membrane 46c, through duct 48c and outlet 49c. The differences between the design of this device and that shown in FIG. 3 comprises the fact that, in this case the device has been provided with a pulyurethane foam coated with silicone oil, which is designated 50. By utilizing such a device the formation of froth in the filtrate is prevented, while any froth 51 already formed is broken down thereby.

Although polyurethane foam with silicone oil is a well-known means for the breaking down of blood froth, it will be clear to those of ordinary skill in this art that other froth-preventing agents could also be used therein.

Turning finally to the embodiment shown in FIG. 5, this device corresponds substantially to that shown in FIG. 4. For this reason, the same reference numerals have again been used, but in this case the letter "c" has been replaced by the letter "d". Thus, filtrate is supplied through inlet 21d, and is withdrawn through outlet 22d. The accumulated gas is discharged through window 48d, and outlet 49d. Any filtrate froth formed therein is broken down by means of polyurethane foam coated with silicone oil, and designated 50d. For practical reasons, it has been inserted in this device in the form of three discs, arranged one on top of another. These discs, in turn, rest on a plate 51d, which is arranged on supporting leg 52d. As a result, the filtrate follows the inner walls of the pressure equalizing device, even if the fluid level happens to be lower than the height of plate 51d. An advantage of this design is thus that duct 48 will normally be immersed in the fluid. In this manner, no condensate can form on the inside of the duct, which is a hazard which may exist, for example, in the embodiment shown in FIG. 4. If the formation of such condensate shall occur, it could cause the inside of the membrane to be blocked for the passage of gas.

It will be understood that the embodiments described herein are merely exemplary and that a person skilled in the art may make many variations and modifications without departing from the spirit and scope of the invention. All such modifications and variations are intended to be included within the scope of the invention as defined im the appended claims.

What we claim is:

1. Apparatus for the measurement of a filtrate separated from a supply of blood and replacement of said filtrate with a replacement fluid as a substitute for said filtrate in said blood comprising measuring means for measuring the amount of said filtrate flowing therethrough, first conduit means for continuously delivering said filtrate to said measuring means, second conduit means for supplying an amount of a replacement fluid as a substitute for said measured amount of said filtrate, pump means associated with said first conduit means for drawing said filtrate through said first conduit means into said measuring means, and pressure equalizing means associated with said first conduit means and located at a point in said first conduit means between said pump means and said measuring means for equalizing the pressure in said filtrate flowing through said first conduit means, whereby the flow of said filtrate through said measuring means is substantially unaffected by pressure variations in said filtrate.

2. The apparatus of claim 1, including filter means for contacting with said supply of blood so as to produce said filtrate therefrom.

3. The apparatus of claim 1, wherein said pressure equalizing means is located at a point in said first conduit means substantially adjacent to said measuring means.

4. The apparatus of claim 1, wherein said pressure equalizing means includes bubble collection means for collecting any gas bubbles contained within said filtrate so as to prevent said gas bubbles from being delivered to said measuring means.

5. The apparatus of claim 1, wherein said pump means comprises a peristaltic pump, whereby said pump means can contact the outer surface of said first conduit means for drawing said filtrate therethrough.

6. The apparatus of claim 1, wherein said measuring means comprises first measuring means, and including second measuring means for measuring the amount of said replacement fluid flowing into said second conduit means.

7. The apparatus of claim 6, including comparison means for comparing the amounts of said filtrate and said replacement fluid measured by said first and second measuring means, respectively.

8. The apparatus of claim 1, wherein said pressure equalizing means comprises first pressure equalizing means, and including second pressure equalizing means, said second pressure equalizing means being associatd with said second conduit means for equalizing the pressure in said replacement fluid flowing through said second conduit means.

9. The apparatus of claim 8, wherein at least one of said first and second pressure equalizing means includes a housing and fluid level control means for maintaining the level of said fluid within said housing at a predetermined level therein.

10. The apparatus of claim 8, wherein at least one of said first and second pressure equalizing means includes froth reduction means for reducing the creation of froth from said fluid therein.

11. The apparatus of claim 1, wherein said pressure equalizing means includes a housing and fluid level control means for maintaining the level of said filtrate within said housing at a predetermined level therein.

12. The apparatus of claim 11 or 9, wherein said liquid level control means comprises membrane means having a first surface and a second surface, said first surface of said membrane means being in contact with said housing, whereby said first surface of said membrane means is accessible to said fluid contained within said housing, said second surface of said membrane means being exposed to the atmosphere, said membrane means being gas permeable and fluid impermeable, whereby said fluid level within said housing can be controlled by the passage of gas through said membrane means.

13. The apparatus of claim 12, wherein said housing includes an outer wall including a window, and wherein said membrane means is contained within said window.

14. The apparatus of claim 13, wherein said outer wall of said housing including said window means is vertically disposed, and wherein said membrane means includes an upper end and a lower end, whereby said fluid level may be controlled substantially between said upper end and said lower end of said membrane means.

15. The apparatus of claim 12, wherein said membrane means is entirely enclosed within said housing.

16. The apparatus of claim 12, including membrane conduit means connecting said second surface of said membrane means to the atmosphere.

17. The apparatus of claim 16, wherein said membrane means is horizontally disposed within said housing.

18. The apparatus of claim 17, wherein said first surface of said membrane means is directed generally upwardly and wherein said second surface of said membrane means is directed generally downwardly.

19. The apparatus of claim 18, wherein said membrane conduit means extends generally vertically downwardly from said second surface of said membrane means, whereby any condensate formed within said membrane conduit means runs downwardly along said membrane conduit means and away from said membrane means.

20. The apparatus of claim 19, wherein said housing for said pressure equalizing means includes a fluid inlet at the upper end thereof, said fluid inlet being in fluid communication with said first conduit means.

21. The apparatus of claim 20, wherein said housing includes froth reduction means therein for reducing the creation of froth from said fluid between said fluid inlet and said membrane means.

22. The apparatus of claim 21, wherein said housing for said pressure equalizing means includes a fluid outlet at the lower end thereof, said fluid outlet being in fluid communication with said first conduit means.

23. The apparatus of claim 1, wherein said pressure equalizing means includes froth reduction means for reducing the creation of froth from said filtrate therein.

24. The apparatus of claim 1, including temperature measuring means for measuring the temperature of said filtrate flowing through said first conduit means.

25. A device for equalizing the pressure of a fluid flowing in a fluid conduit, said device comprising a housing in fluid communication with said fluid conduit, fluid level control means for maintaining the level of said fluid within said housing at a predetermined level therein, said liquid level control means comprising membrane means having a first surface and a second surface, said first surface of said membrane means being in contact with the inside of said housing, whereby said first surface of said membrane means is accessible to said fluid contained within said housing, said second surface of said membrane means being exposed to the atmosphere, said membrane means being gas permeable and fluid impermeable, whereby said fluid level can be controlled by the passage of gas through said membrane means, and condensate removal means for removal of any condensate formed relative to said second surface of said membrane means so as to prevent said condensate from interfering with said passage of said gas through said membrane means.

26. The apparatus of claim 25, wherein said condensate removal means includes membrane conduit means connecting said second surface of said membrane means to the atmosphere.

27. The apparatus of claim 26, wherein said membrane means is horizontally disposed within said housing.

28. The apparatus of claim 27, wherein said first surface of said membrane means is directed generally upwardly and wherein said second surface of said membrane means is directed generally downwardly.

29. The apparatus of claim 27, wherein said membrane conduit means extends generally vertically downwardly from said second surface of said membrane means, whereby any condensate formed within said membrane conduit means runs downwardly along said membrane conduit means and away from said membrane means.

* * * * *